United States Patent [19]

Gorton

[11] Patent Number: 5,009,641
[45] Date of Patent: Apr. 23, 1991

[54] PATIENT-CONTROLLED ANALGESIA SECURITY ATTACHMENT FOR A MEDICATION INFUSION SYSTEM

[75] Inventor: Lanny A. Gorton, Sunland, Calif.
[73] Assignee: Pacesetter Infusion, Ltd., Sylmar, Calif.
[21] Appl. No.: 279,466
[22] Filed: Dec. 2, 1988
[51] Int. Cl.5 ............................................. A61M 5/00
[52] U.S. Cl. .................................. 604/131; 604/151; 128/DIG. 12; 417/360
[58] Field of Search ................... 417/360, 474–477; 128/DIG. 12, DIG. 13; 604/131, 151, 153–155, 110, 111

[56] References Cited

U.S. PATENT DOCUMENTS

| | | | |
|---|---|---|---|
| 3,731,679 | 5/1973 | Wilhelmson et al. | 128/DIG. 12 |
| 3,927,955 | 12/1975 | Spinosa et al. | 417/477 |
| 4,187,057 | 2/1980 | Xanthopoulos | 604/153 |
| 4,314,567 | 2/1982 | Cannon | 128/DIG. 12 |
| 4,447,234 | 5/1984 | Mayfield | 604/152 |
| 4,468,222 | 8/1984 | Lundquist | 417/360 |
| 4,479,761 | 10/1984 | Bilstad et al. | 604/153 |
| 4,496,351 | 1/1985 | Hillel et al. | 128/DIG. 13 |
| 4,565,542 | 1/1986 | Berg | 604/151 |
| 4,627,839 | 12/1986 | Young | 128/DIG. 12 |
| 4,653,987 | 3/1987 | Tsuji et al. | 417/360 |
| 4,688,545 | 8/1987 | Srebnik et al. | 417/360 |
| 4,756,706 | 7/1988 | Kerns et al. | 604/66 |

FOREIGN PATENT DOCUMENTS

| | | | |
|---|---|---|---|
| 8203254 | 9/1982 | PCT Int'l Appl. | 417/476 |
| 2165312 | 4/1986 | United Kingdom | 128/DIG. 12 |

Primary Examiner—John D. Yasko
Assistant Examiner—Anthony M. Gutowski
Attorney, Agent, or Firm—Leslie S. Miller

[57] ABSTRACT

A device for use as an attachment for use with a main pump unit containing a prime mover and a control system for controlling the operation of a disposable cassette containing a fluid pump which is mounted on the main pump unit is disclosed which includes both a compartment for securely storing the medication supply and means for preventing either the cassette or the fluid line between the storage compartment and the cassette from being removed or tampered with. The device is locked onto the main pump unit with a single key operated lock which also locks the cassette in position on the main pump unit, the compartment for storing the medication supply, and a cover sealing the fluid line. The system is compact, and is capable of being used with a variety of fluid sources including both syringes and bags.

24 Claims, 7 Drawing Sheets

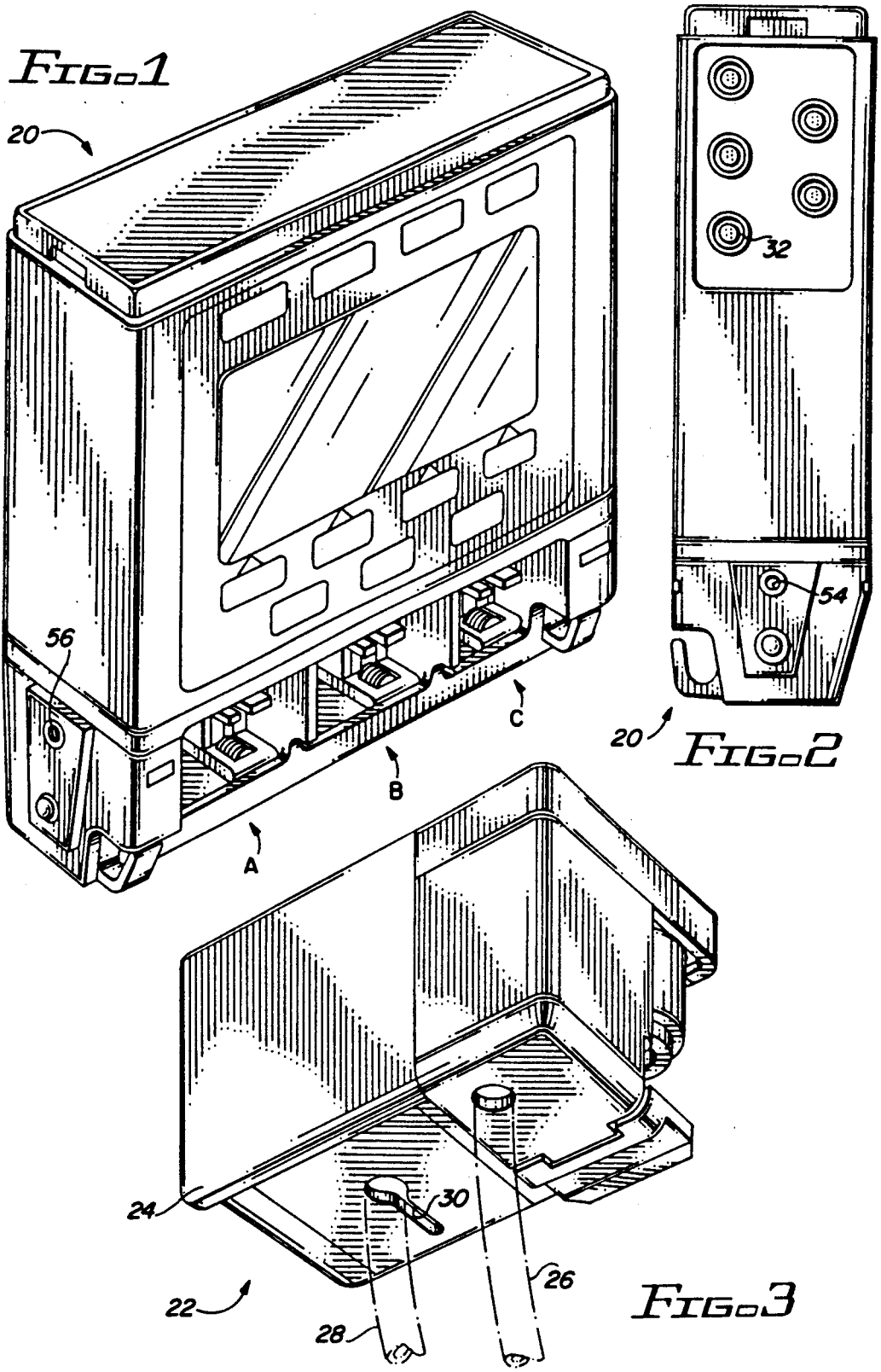

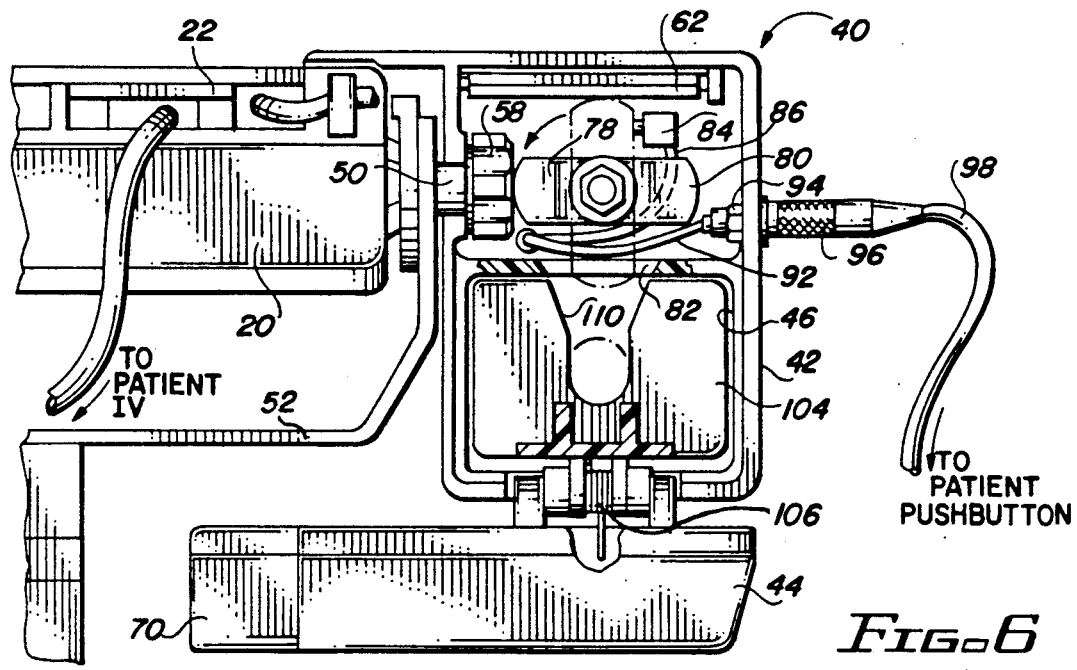
FIG. 6
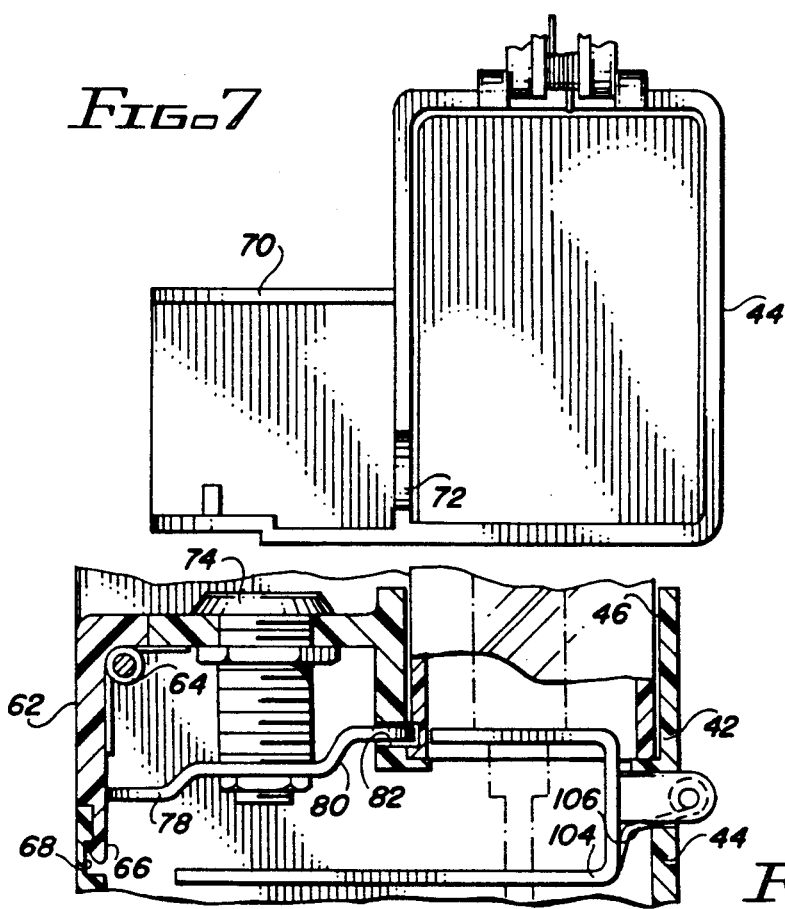
FIG. 7
FIG. 8A

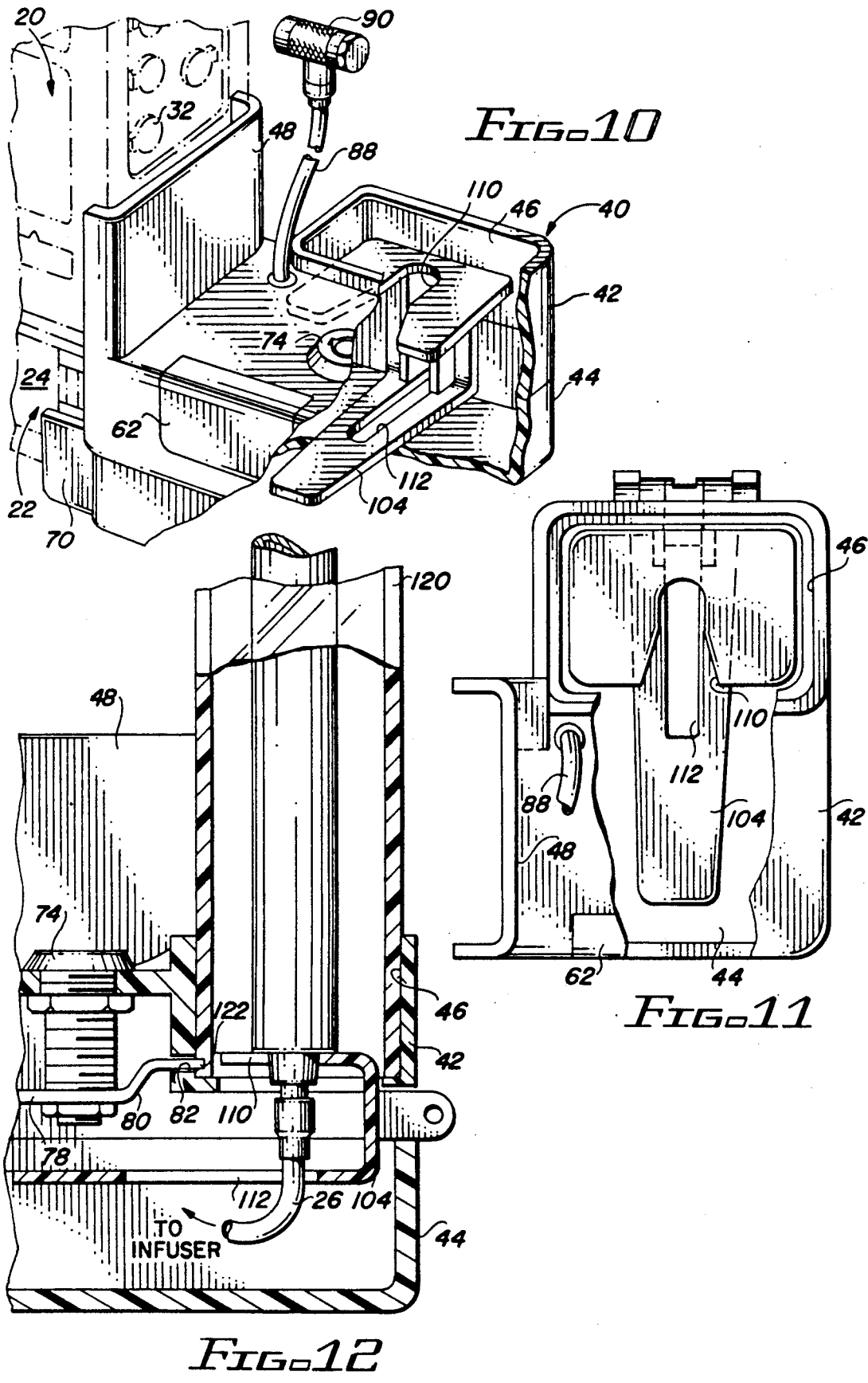

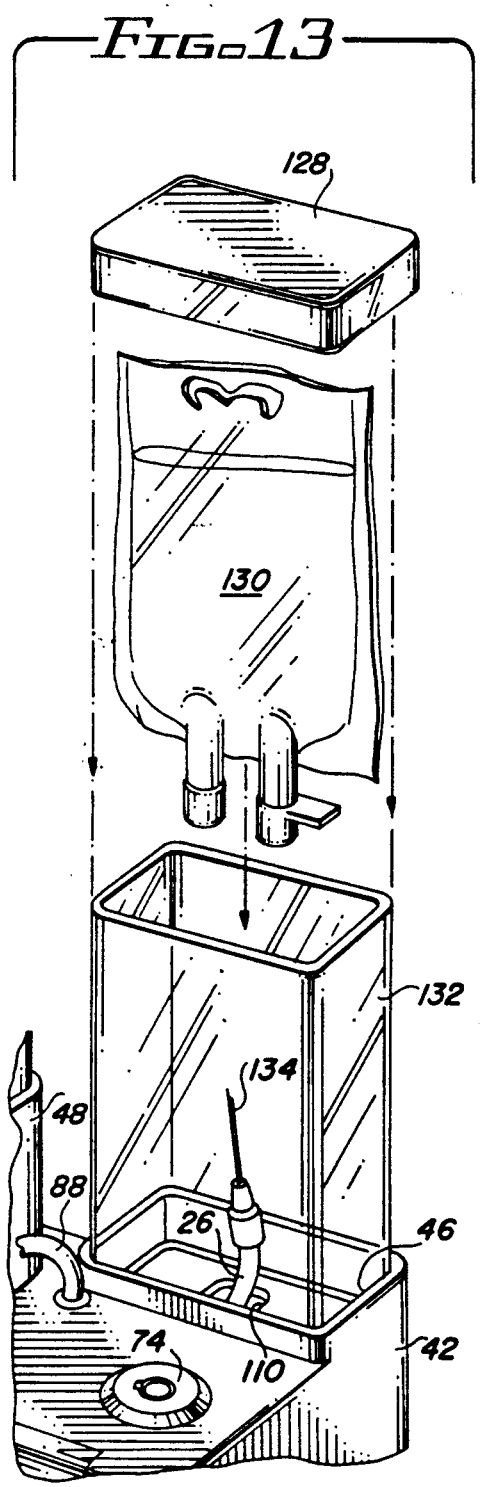
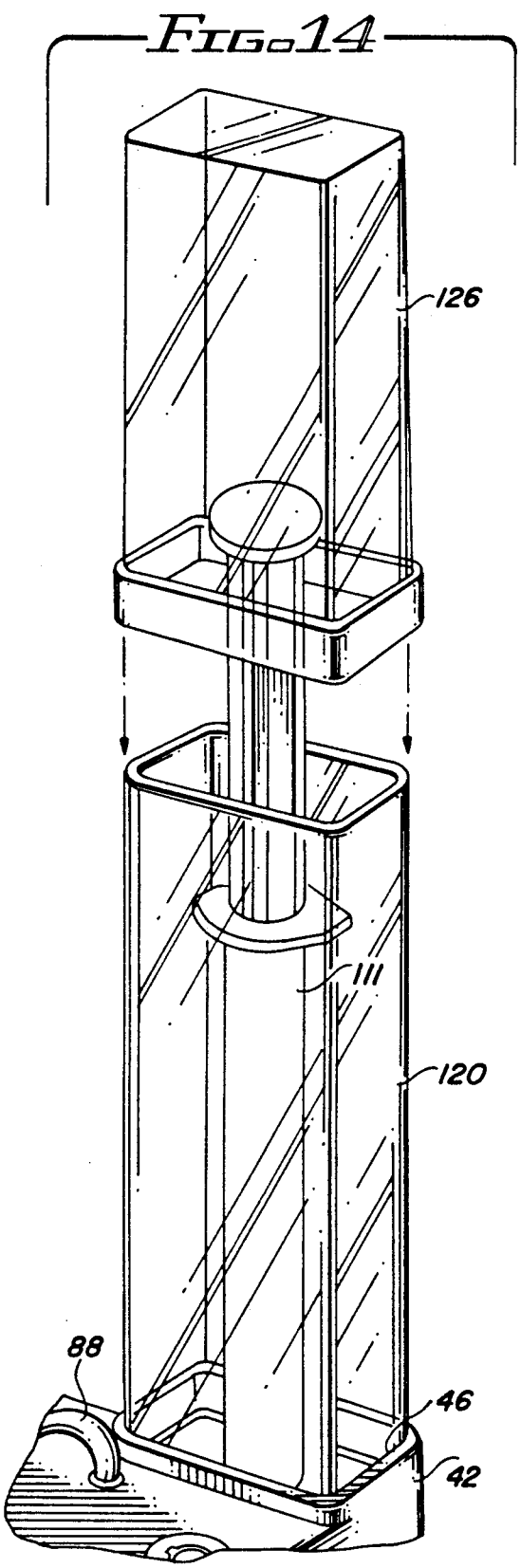

PATIENT-CONTROLLED ANALGESIA SECURITY ATTACHMENT FOR A MEDICATION INFUSION SYSTEM

BACKGROUND OF THE INVENTION

Field of the Invention—The present invention relates generally to an electromechanical system for infusing analgesia or like medication into a patient on demand by the patient, and more particularly to an attachment for use with a main pump unit containing a prime mover and a control system for controlling the operation of a disposable cassette containing a fluid pump which is mounted on the main pump unit, the attachment including both a compartment for securely storing the medication supply and means for preventing either the cassette or the fluid line between the storage compartment and the cassette removed or tampered with.

One of the longest-standing objectives of medicine has always been the efficacious alleviation of chronic and incessant pain. It has often been difficult to effectively control such severe pain even though a number of highly effective painkilling medications are widely known. Since it is difficult for a physician to objectively measure pain in a patient, it has remained difficult to accurately control pain in a manner affording consistently helpful relief to the patient.

Dosage of painkilling medication is based on general dosage guidelines which minimize dosage to prevent side effects of the drug. Such general guidelines often provide inadequate assistance since the effects of any particular medication may vary widely between patients. Accordingly, pain is often either overcontrolled or undercontrolled in many patients, with the corresponding side effects of either a sedative effect or an inadequate diminution in the level of pain, respectively.

In the past there have been two primary techniques which have been used to deliver drugs to a patient- oral ingestion and intramuscular injection. The first technique is accomplished by having the patient swallow pills or a liquid. The second such technique is through an intramuscular injection, or shot, using a syringe and needle which, like oral administration, delivers a large dosage at relatively infrequent intervals to the patient. These techniques are generally unsatisfactory, particularly when the drug being administered is a painkiller which is potentially lethal, has negative side effects when delivered in a large dosage, or must be delivered more or less continuously to achieve the desired therapeutic effect.

In the administration of painkilling medication by either oral ingestion or by intramuscular injection, a sufficient amount of the medication is administered to last at least several hours. This typically initially overmedicates the patient, with a steady diminution in effect representing increasing pain until another injection is administered and takes effect. This problem may result in smaller doses or injections being given at more frequent intervals, a compromise approach not yielding wholly satisfactory results.

As an alternative to these two techniques of administering medication to a patient, the relatively recent addition of patient-controlled analgesia (PCA) pumps has come as a welcome improvement. PCA pumps may be utilized to administer painkilling drugs intravenously to a patient in smaller, metered doses at frequent intervals on demand by the patient, within limits prescribed by a physician. Since the medication is administered directly into the bloodstream, relief is virtually immediate. PCA pump therapy may be electronically controlled to deliver precise, metered doses immediately upon demand by the patient, thereby providing a beneficial administration of painkilling medication to the patient whenever it is needed.

Since the overmedication associated with intramuscular or oral delivery is avoided, in some patients significantly less painkilling medication is required with PCA pump therapy than with conventional therapies. PCA pumps are particularly effective in treating terminally ill patients, and have been used effectively for intraspinal and subcutaneous infusions. Recent advances in equipment have allowed the PCA pump to be used in a home care setting in addition to its use in a hospital setting.

A multi-purpose infusion system capable of operating as a PCA pump is disclosed in U.S. patent application Ser. No. 127,333, now U.S. Pat. No. 4,832,299 entitled "Disposable Cassette for a Medication Infusion System," and assigned to the assignee of the present application, which application is hereby incorporated herein by reference. In this system, a disposable cassette contains a piston-type fluid pump and active valves to pump fluid, with the piston and valves in the cassette being operated by a mechanical drive system located in and controlled by a main pump unit. The cassette includes a slide latch for latching the cassette in place on the main pump unit, which slide latch also closes the fluid path before the cassette is installed and when it is removed, the slide latch only being opened when the cassette is properly installed on the main pump unit.

The cassette has an inlet tube designed to be connected to a fluid reservoir or other fluid source, and a fluid outlet tube designed to be connected to an administration set for delivery to a patient. The main pump unit has one of its three channels which may be configured as a PCA pump, and an input to the main pump unit may be used as the channel to actuate the pump at the patient's request. Administration is controlled by specifying demand dose volume (bolus volume), lockout interval (the minimum time between administration of doses, also called the refractory period), and maximum dosage over a given time period (four hours, for example). Additional commands which may optionally be utilized are a loading bolus (administered at the beginning of PCA therapy to quickly increase serum concentration of the drug) and continuous infusion (a basal rate to maintain an appropriate serum level, thereby minimizing the number of demand doses).

The system may be used to administer narcotic drugs such as morphine, meperidine, and fentanyl. It will of course be realized by those skilled in the art that such drugs are controlled substances, normally kept under lock and key. As such, the use of these drugs in a PCA pump requires a substantial amount of the drug to be located in a reservoir accessible by the PCA pump. It is therefore necessary to provide a sufficient level of security to prevent theft of the drug.

A device used to secure the infusion system described above to an IV pole is disclosed in U.S. patent application Ser. No. 128,744, now U.S. Pat. No. 4,872,813 entitled "Clamp Fixture," and assigned to the assignee of the present application, which application is hereby incorporated herein by reference. However this clamp is designed only to secure the main pump unit to the IV pole, and does not secure the medication being pumped by the system.

It is therefore the primary object of the present invention to provide a mechanism for securing the supply of medication in the reservoir located near the PCA pump. In order to accomplish this purpose, the reservoir itself must first be secured to prevent it from being stolen or removed from the location of the PCA pump. Since the PCA main pump unit discussed above is secured to an IV post, it is an objective of the present invention to secure the medication to the main pump unit to prevent its theft or removal.

In order to make not just the medication reservoir but the entire fluid system secure, it is also vital to protect the fluid line between the medication reservoir and the cassette. The present invention must also accomplish this end, since if the fluid line is left unprotected, it would be simple for an unauthorized individual to open the fluid line between the medication reservoir and the cassette and drain the medication reservoir. Accordingly, it is an objective of the present invention to protect the integrity of the fluid line between the medication reservoir and the cassette.

The design of the cassette allows the system to be primed when the cassette is removed from the main pump unit. The priming operation allows medication to flow freely through the cassette, a situation which would be potentially deadly were it to occur with an administration set delivering medication from the cassette to the patient. Accordingly, it is a further objective of the present invention that it prevent the unauthorized removal of the cassette from the main pump unit.

The security provisions which are objectives of the present invention should all operate to prevent both any action by a patient or any tampering by an unauthorized individual from violating the security of the medication being administered. The security attachment of the present invention must be relatively compact in size, yet be capable of holding the several different sizes and configurations of medication containers. Specifically, the device must be capable of containing various size syringes, as well as small flexible plastic medicine bags. In addition, the device must be relatively inexpensive of construction, to thereby afford it the most advantageous market advantage. Finally, the system of the present invention must accomplish all of the aforesaid objectives and advantages without incurring any relative disadvantage.

SUMMARY OF THE INVENTION

The disadvantages and limitations of the background art discussed above are overcome by the present invention. With this invention, a security containment device is mounted on the side of the main pump unit. The security containment device includes a lock, which will prevent the removal of the security containment device from the main pump unit without the use of an appropriate key. Since the main pump unit is locked to an IV pole by the use of the above-identified incorporated by reference patent application entitled "Clamp Fixture," this secures the security containment device as well to the IV pole.

The security containment device has a storage compartment which may hold various size syringes, as well as small flexible plastic medicine bags. The storage compartment in the preferred embodiment consists of several interchangeable capped tubes of different sizes, which may be locked onto the security containment device. The key lock used to secure the security containment device to the main pump unit may also serve to lock any one of the storage compartments to the security containment device. Alternately, the storage compartments may have one-way snap locks which can only be released from the device when the security containment device is unlocked and the snap lock is released from the inside.

The security containment device of the present invention, when mounted onto the main pump unit, fits over a portion of the cassette mounted in the main pump unit, thereby retaining the cassette in place. Since the cassette cannot be removed from the main pump unit without first removing the security containment device, a free flow condition through the cassette caused by tampering is prevented. The security containment device of the present invention also completely contains the fluid line between the medication reservoir and the cassette, thus preventing the fluid line between the medication reservoir and the cassette from being opened and the medication reservoir from being drained.

The security containment device of the present invention also includes an electrical cable to be connected to the electrical input connector on the main pump unit, and a removeable actuation cable with a switch for actuation by the patient. The actuation cable is of sufficient length to reach a patient, so that the patient need only squeeze the button on the switch to request a demand dose or bolus. The lock in the security containment device must be in the locked position for the switch to operate the main pump unit.

It is therefore apparent that the present invention provides a mechanism for securing the supply of medication in the reservoir located near the PCA pump. In accomplishing this purpose, the reservoir itself is secured to the PCA pump to prevent it from being stolen or removed. Since the main pump unit is secured to an IV post, the present invention by securing the medication to the main pump unit effectively prevents its theft or removal.

The system of the present invention also protects the integrity of the fluid line between the medication reservoir and the cassette in order to make the entire fluid system secure, thereby preventing an unauthorized individual from opening the fluid line between the medication reservoir and the cassette and draining the medication reservoir. The present invention also prevents the unauthorized removal of the cassette from the main pump unit, thus preventing a potentially deadly free flow condition through the cassette from occurring.

The security provisions of the present invention thus operate to prevent both any action by a patient or any tampering by an unauthorized individual from violating the security of the medication being administered. The security attachment of the present invention is relatively compact in size, yet is capable of holding any of the several different sizes and configurations of medication containers, including various size syringes and small flexible plastic bags. In addition, the device is relatively inexpensive to manufacture, thereby affording it the most advantageous market advantage. Finally, the system of the present invention accomplishes all of the aforesaid objectives and advantages without incurring any relative disadvantage.

DESCRIPTION OF THE DRAWINGS

These and other advantages of the present invention are best understood with reference to the drawings, in which:

FIG. 1 is a perspective view of a main pump unit similar to the one described in the above-identified incorporated by reference patent application entitled "Disposable Cassette for a Medication Infusion System;"

FIG. 2 is a side view of the main pump unit shown in FIG. 1, showing electrical input connectors with their hinged, spring-loaded protective caps removed for clarity, one of which electrical input connectors is used to provide electrical signals to the main pump unit to request delivery of demand doses or boluses of medication;

FIG. 3 is a perspective view of a disposable cassette similar to the one described in the above-identified incorporated by reference patent application entitled "Disposable Cassette for a Medication Infusion System," showing the inlet and outlet tubes in phantom lines;

FIG. 6 is a sectional view of the security containment device shown in FIG. 5, showing the hinged lower housing opened for visibility;

FIG. 7 is a sectional view showing the interior of the lower housing of the security containment device;

FIG. 8A is a first sectional view of the lock mechanism of the security containment device in the locked position, holding the syringe tube mounted in place in the upper housing and preventing the latch from being operated to open the lower housing;

FIG. 10 is a perspective cutaway view of the security containment device of the present invention showing the hinged and spring-loaded syringe retainer shown in FIG. 10;

FIG. 11 is a top cutaway view of the security containment device of the present invention showing the syringe retainer;

FIG. 12 is a sectional view showing a syringe located mounted in the security containment device of the present invention, which syringe is retained by the syringe retainer shown in FIGS. 10 and 11;

FIG. 13 is a perspective view of the syringe tube used with a short tube cap to hold a small plastic medicine bag; and FIG. 14 is a perspective view of the syringe tube used with a extended tube cap to hold a large syringe.

DETAILED DESCRIPTION OF THE PREFERRED EMBODIMENT

Figure 4:
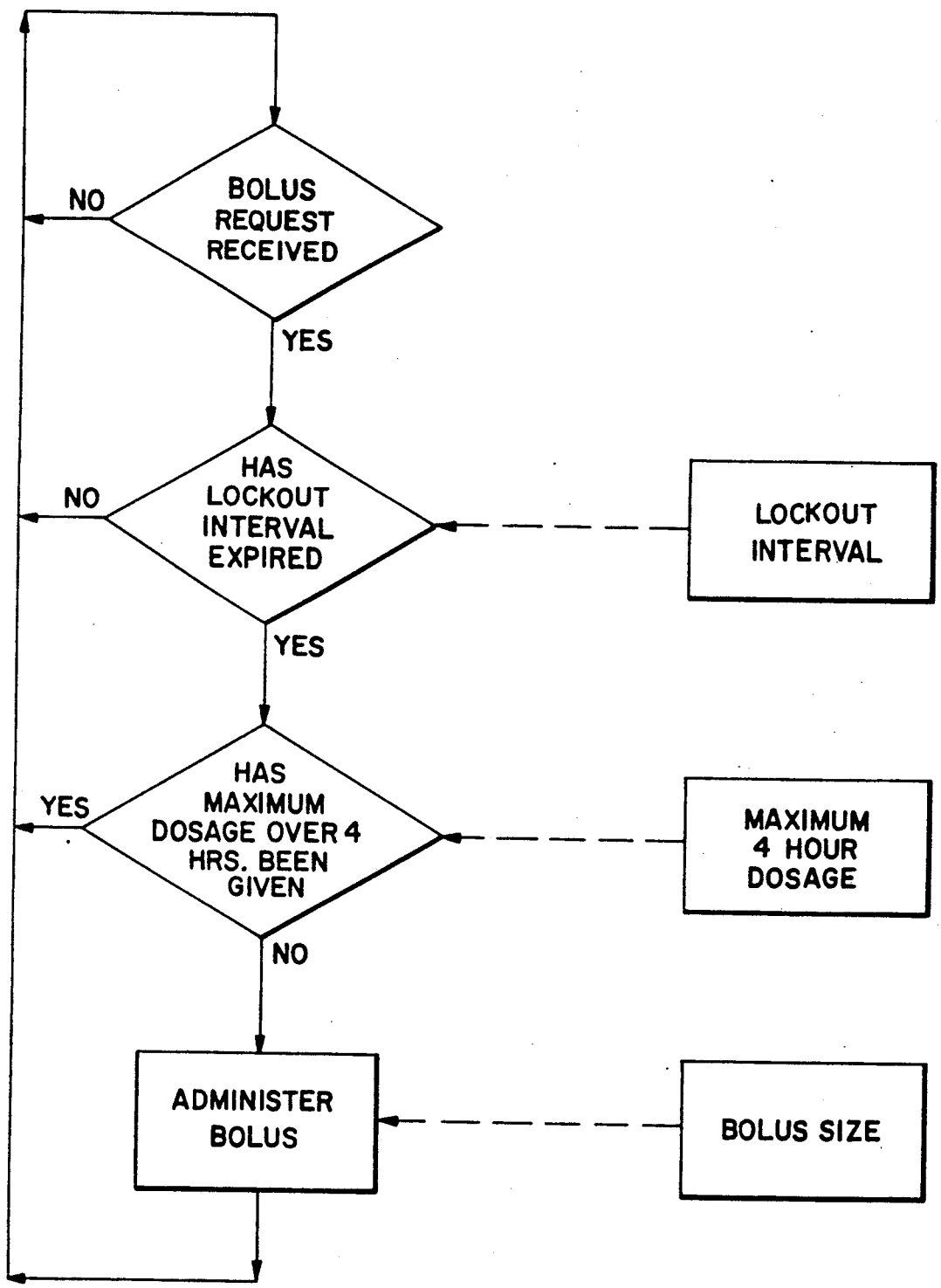
FIG. 4 is a flow diagram illustrating a basic PCA routine which may be performed by the main pump unit and cassette shown in FIGS. 1 through 3.

Before discussing in detail the PCA security containment device of the present invention, it is appropriate to briefly review the main pump unit the preferred embodiment PCA attachment is designed to be mounted onto. This discussion describes briefly the installation of a cassette onto the main pump unit and the operation of the device to pump fluid. For further details about the construction and operation of the main pump unit and the disposable cassette, the reference incorporated above entitled "Disposable Cassette for a Medication Infusion System" provides,in great detail the details of construction of both the cassette and the main pump unit.

A main pump unit 20 is shown in FIGS. 1 and 2, and a disposable cassette 22 is shown in FIG. 3. The main pump unit 20 has three bays for accepting up to three cassettes 22, with the bays being labeled A, B, and C. The bay labeled as C is the position in which the cassette 22 will be inserted to be used as a PCA pump. The cassette 22 contains a piston-type fluid pump and active valves to pump fluid, with the piston and valves in the cassette 22 being operated by a mechanical drive system located in and controlled by the main pump unit 20.

The cassette 22 has a slide latch 24 which serves both to lock the cassette 22 in place in one of the bays A, B, or C in the main pump unit 20, and to control the flow of fluid through the cassette 22. The cassette 22 has an inlet tube 26 (shown in phantom lines) used to supply fluid to the cassette 22, and an outlet tube 28 (shown in phantom lines) used to carry fluid away from the cassette 22. The inlet and outlet tubes 26 and 28 typically have luer connectors (not shown) on the ends thereof to provide for easy connection.

The slide latch 24 has two positions: a locked position in which it is flush with the front of the cassette 22, as shown in FIG. 3, and an unlocked position in which it is pulled back from the front of the cassette 22 (not shown). With the slide latch 24 pulled back from the front of the assembled cassette 22 in the unlocked position, an elongated, tear-shaped aperture 30 in the slide latch 24 will close the outlet tube 28, preventing fluid from flowing through the cassette 22. The inlet tube 26 is connected to a fluid source such as an IV bag (not shown), and the outlet tube 28 is connected to a fluid delivery device such as an injection set (not shown), the use of which is well known in the art. The slide latch 24 is moved to its locked position, and fluid fills the lines, the cassette 22, and the injection set. By tapping or shaking the cassette 22 any residual air bubbles will flow out through the line. The slide latch 24 is then pulled back to its unlocked position to close the outlet tube 28, and the system is in a primed condition with the cassette 22 ready to be installed onto the main pump unit.

With the rear-most edge of the cassette 22 tilted upward, the cassette 22 is inserted into bay C. When the cassette 22 is pushed fully back in place, the front of the cassette 22 is tilted upward. The slide latch 24 may then be pushed forward into its locked position. Simultaneously, the outlet tube 28 will be opened, but fluid will not flow through the outlet tube 28 since the cassette 22 is installed on the main pump unit 10. The cassette 22 will thus be held in position on the main pump unit 20 until the slide latch 24 is again pulled back to its unlocked position, releasing the cassette 22.

The C channel in the main pump unit 20 may be configured as a PCA pump, and a signal supplied to an input connector 32 on the main pump unit 20 may be used as the channel to actuate the pump at the patient's request. In this system, administration is controlled by specifying demand dose volume (bolus volume), lock-out interval (the minimum time between administration of doses, also called the refractory period), and maximum dosage over a given time period (four hours, for example). Additional commands which may optionally be utilized are a loading bolus (administered at the beginning of PCA therapy to quickly increase serum concentration of the drug) and continuous infusion (a basal rate to maintain an appropriate serum level, thereby minimizing the number of demand doses).

Referring briefly to FIG. 4, the operation of a PCA device is shown in simplified fashion. When a bolus or demand dose request is received from the patient, the device checks to see if the lockout interval or refractory period has expired. If it has not, the device returns to the beginning of the loop to wait for a further bolus or demand dose request. This indicates that the patient has requested a demand dose too soon after the previous dose, with the relevant period being the lockout interval or refractory period set by the doctor.

On the other hand, if the lockout interval or refractory period has expired, the device then checks to see if the maximum cumulative dosage over the previous 4 hours (or other sliding window time period) would be exceeded by the bolus or demand dose requested. If the maximum cumulative dosage over the previous 4 hours would be exceeded by the bolus or demand dose requested, the device returns to the beginning of the loop to wait for a further bolus or demand dose request. This indicates that the patient has requested a cumulative dosage over the previous 4 hours which would exceed the maximum 4 hour dosage set by the doctor.

If, however, the maximum cumulative dosage over the previous 4 hours would not be exceeded by the bolus or demand dose requested, the bolus or demand dose is administered to the patient. The device then returns to the beginning of the loop to wait for a further bolus or demand dose request. When a bolus or demand dose is administered, the information stored on the lockout interval and the cumulative dosage over the previous 4 hours will be updated. If a loading bolus is used and/or continuous infusion is elected, the information on dosage administered will also be reflected in the information stored on the cumulative dosage over the previous 4 hours.

Figure 5:
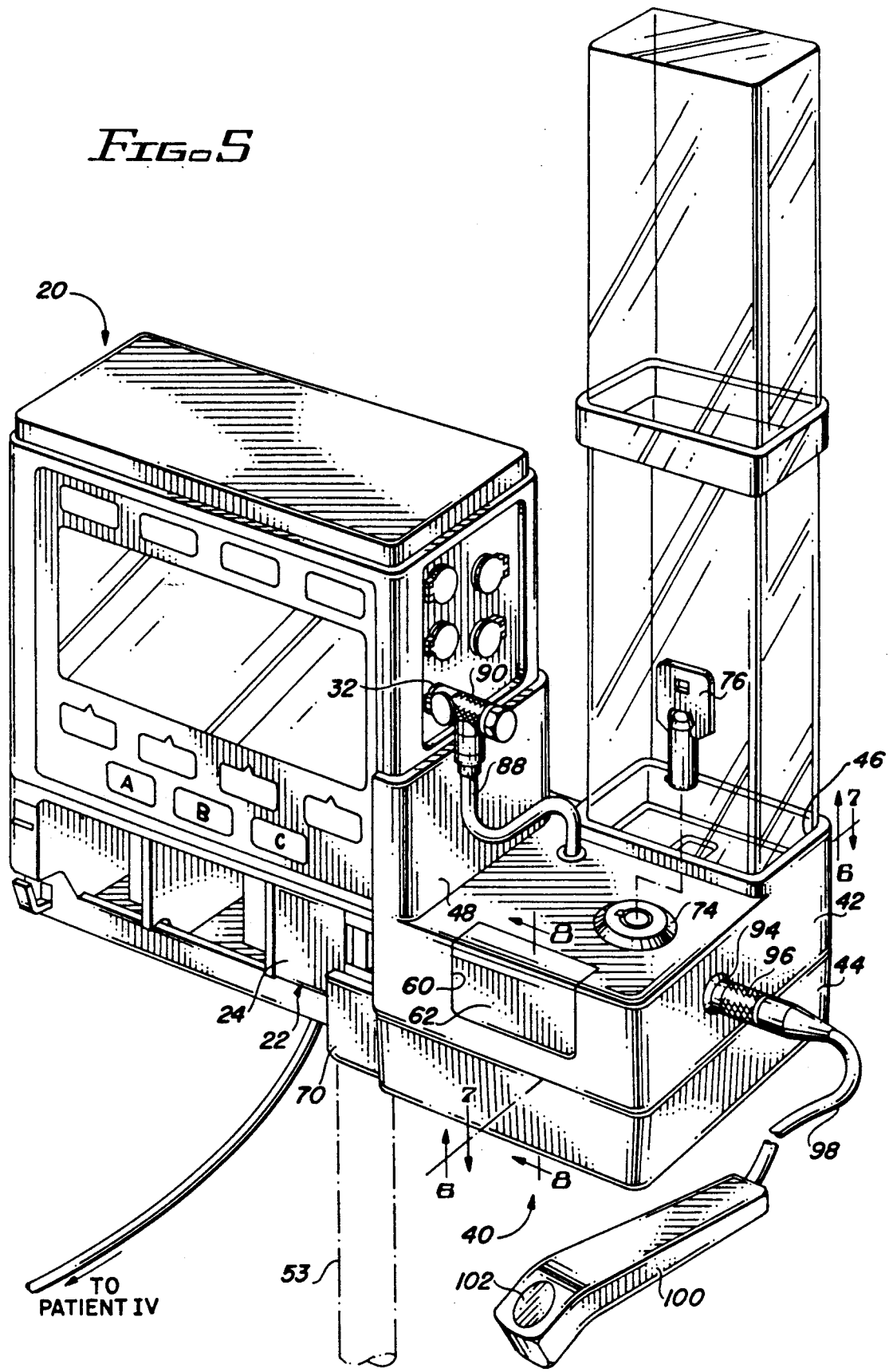
FIG. 5 is a perspective view of the security containment device of the present invention mounted on the main pump unit shown in FIGS. 1 and 2, which main pump unit contains the cassette shown in FIG. 3 mounted in drive bay C.

Referring now to FIG. 5 the preferred embodiment of a security containment device 40 constituting the present invention is illustrated attached to the side of the main pump unit 20 adjacent bay C, in which the cassette 22 is mounted in a locked position. The security containment device 40 includes an upper housing 42 and a lower housing 44, both of which are essentially rectangular in configuration. The upper housing 42 includes a rectangular opening 46 on the top and near the back thereof, which opening 46 is to receive one of a plurality of interchangeable storage compartments, which will be described in detail below.

Figure 9:
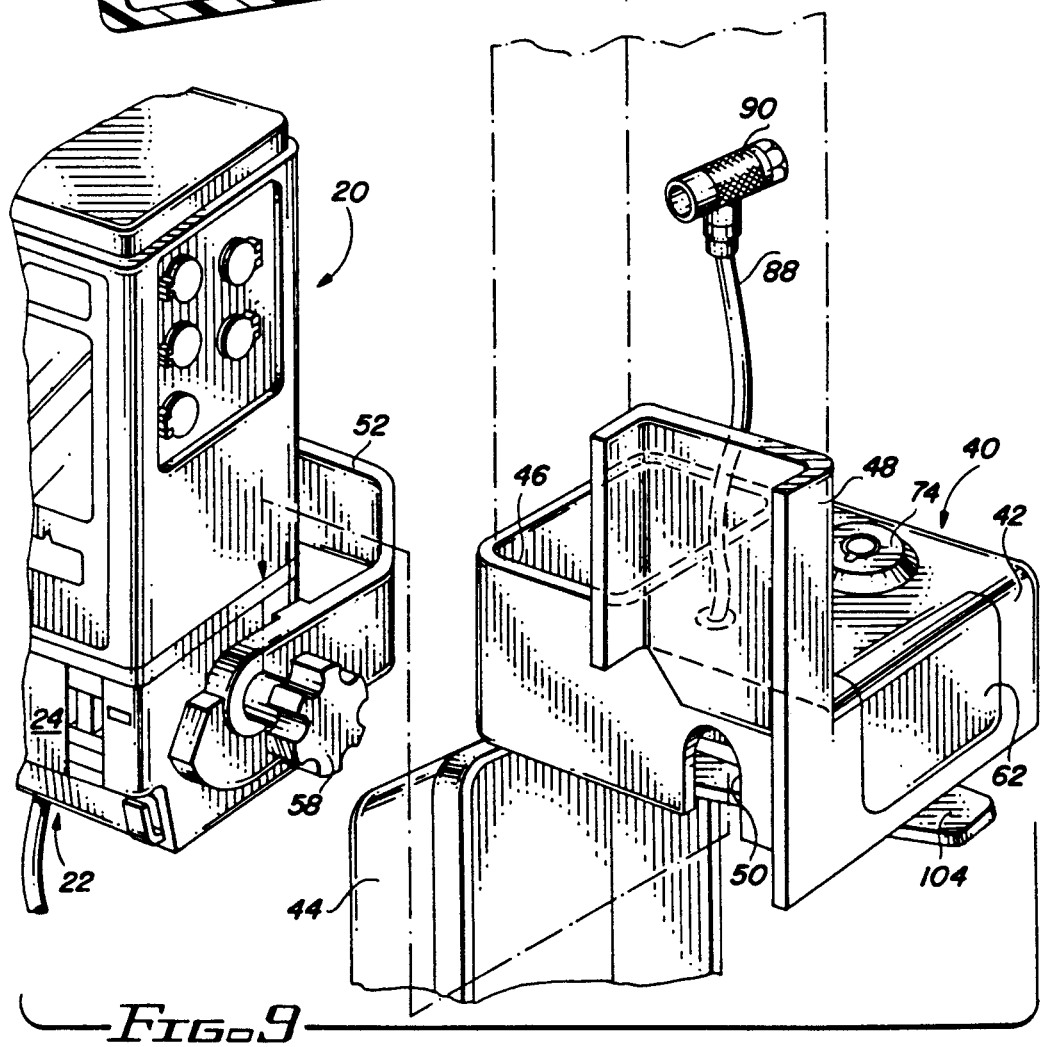
FIG. 9 is a perspective view showing the side of the security containment device of the present invention which is mounted on the side of the main pump unit.

On the left side of the upper housing 42 is a horizontally extending U-shaped plate 48, which plate 48 is contoured to engage the right side of the main pump unit 20. The upper housing 42 has a slot 50 located on the bottom of the left side thereof, as best shown in FIG. 9. The slot 50 is used to retain the upper housing 42, and the entire security containment device 40, in position on the main pump unit 20.

Note that the main pump unit 20 is supported by a clamp fixture 52 (partially shown in FIG. 9) which is in turn locked to an IV pole 53 (shown in phantom lines in FIG. 1) by the use of the clamp device described in the above-identified incorporated by reference patent application entitled "Clamp Fixture." The clamp fixture 52 is normally secured to the main pump unit 20 by bolts (not shown) screwed into threaded apertures 54 and 56 (FIGS. 1 and 2) in the main pump unit 20. The security containment device 40 uses instead of the standard bolt screwed into the threaded aperture 54 (FIG. 2) on the right side of the main pump unit 20 a bolt having a knob 58 mounted thereon, as shown in FIG. 9.

The slot 50 in the upper housing 42 is placed over the shaft of the knob 58, and the knob 58 is turned to screw into the main pump unit 20, thus securing both the upper housing 42 and the clamp fixture 52 therebetween, as best shown in FIG. 6. It will be appreciated by those skilled in the art that when the lower housing 44 is closed with respect to the upper housing 42, the knob 58 will be secured inside the upper and lower housings 42 and 44, thus securing the assembly including the main pump unit 20, the security containment device 40, and the clamp fixture 52 together. Since the clamp fixture 52 may be locked onto an IV pole 53, securing the upper housing 42 to the lower housing 44 will accordingly secure the main pump unit 20 and the security containment device 40 to the IV pole 53.

Figure 8B:
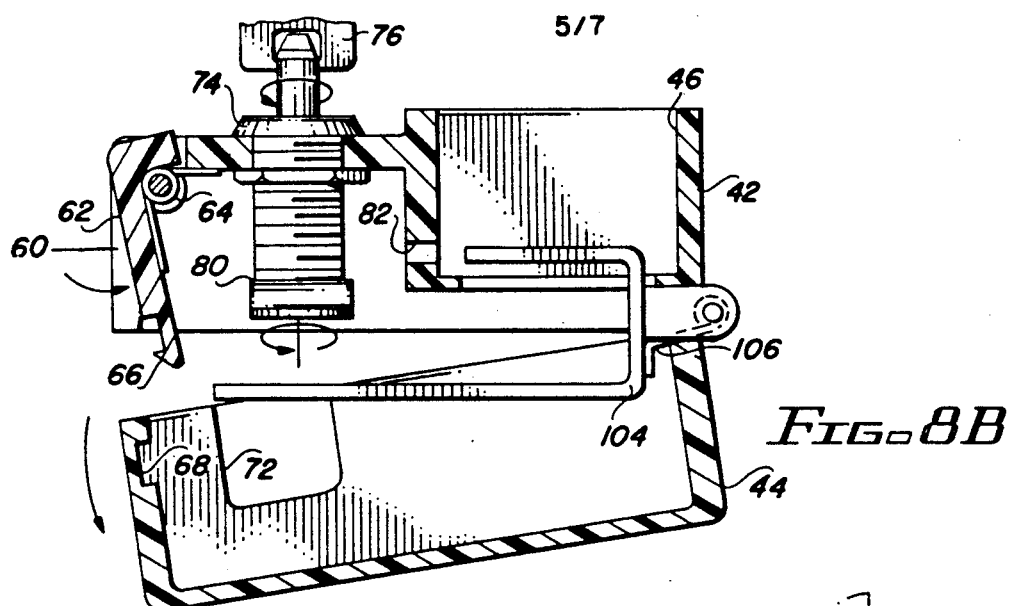
FIG. 8B is a second sectional view of the lock mechanism of the security containment device in the unlocked position, allowing the syringe tube to be removed from the upper housing and allowing the latch to be operated to open the lower housing.

As shown in FIGS. 6 and 8B, the lower housing 44 is hingedly attached at the back thereof to the back of the upper housing 42, in a manner allowing the lower housing 44 to swing down when released. The upper housing 42 has an aperture 60 located at the front and top thereof, which aperture 60 has a latch member 62 mounted therein. The latch member 62 is hingedly mounted at the top thereof to the interior of the upper housing 42. A spring 64 (FIG. 8A) biases the latch member 62 outwardly to a position essentially flush with the exterior of the upper housing 42. The latch member 62 has at the bottom thereof a tapered catch 66, which is designed to cooperated with a notch 68 in the interior of and at the top and front of the lower housing 44.

When the lower housing 44 is pushed shut, the top front edge of the lower housing 44 will push the tapered catch 66 of the latch member 62 backward. As the lower housing 44 closes completely on the upper housing 42, the tapered catch 66 of the latch member 62 will engage the notch 68 in the lower housing 44, holding the lower housing 44 in a closed position with respect to the upper housing 42, as shown in FIG. 8A. To open the lower housing 44, the latch member 62 is pushed inwardly against the force of the spring 64 to move the tapered catch 66 away from contact with the notch 68, releasing the lower housing 44 as shown in FIG. 8B.

Referring again to FIG. 1, note that when the lower housing 44 is in its closed position with respect to the upper housing 42, a U-shaped extension 70 from the left side of the lower housing 44 extends over in front of the cassette 22. The far left edge of the U-shaped extension 70 from the left side of the lower housing 44 extends over the slide latch 24 to prevent it from being pulled out to its unlocked position. Thus, when the lower housing 44 is closed, it is impossible to remove the cassette 22 in bay C of the main pump unit 20. This also prevents a potentially deadly free flow condition through the cassette from occurring.

Referring now to FIG. 7, note that the lower housing 44 has a notch 72 located on the left side near the front thereof. The notch 72 allows a segment of tubing to extend from the interior of the upper and lower housings 42 and 44 to the cassette 22. This segment of tubing would be the inlet tube 26 leading to the cassette 22. When the lower housing 44 is in its closed position, the inlet tube 26 would be protected by the configuration of the U-shaped extension 70 from the left side of the lower housing 44, which U-shaped extension 70 fits closely over the right bottom portion of the main pump unit 20. The security containment device 40 thus protects the integrity of the fluid line between the medication reservoir and the cassette 22, thereby preventing the fluid line from being breached between the medication reservoir and the cassette and draining the medication reservoir.

As shown in FIG. 1, a key-type lock 74 is located in the top of the upper housing 42, which lock 74 may be operated by a key 76. The lock 74 operates a first arm 78 and a second arm 80, both of which arms 78 and 80 are mounted onto the bottom of a shaft turned by the lock 74 inside the upper housing 42. The arms 78 and 80 are mounted on the lock 74 180 degrees apart, and the lock 74 may turn 90 degrees from a locked position to an unlocked position. In the locked position, the first arm 78 is directed toward the front of the security containment device 40, and the second arm 80 is directed toward the rear. In the unlocked position, first arm 78 is directed toward the left side of the security containment device 40, and the second arm 80 is directed toward the right side.

In the locked position, the first arm 78 bears against the latch member 62, preventing it from being pressed inwardly to release the lower housing 44. When the lock 74 is turned to the unlocked position, the first arm 78 moves away from the latch member 62, allowing it to be pressed inwardly to release the lower housing 44. In the unlocked position, the first arm 78 bears against the knob 58, preventing it from being turned. To turn the knob 58 to release the security containment device 40 from the main pump unit 20, the lock 74 must be returned to its locked position after the lower housing 44 is opened and with the lower housing 44 remaining open.

A slot 82 is located in the front wall defining the opening 46 in the upper housing 42, as best shown in FIGS. 6, 8A, and 8B. The slot 82 allows the second arm 80 to move therein as it is turned from a unlocked position to a locked position. In the locked position shown in phantom lines in FIG. 6, it should be noted that the second arm 80 extends beyond the back of the front wall defining the opening 46 into the opening 46. This will function to retain the chosen medication storage compartment, as will become evident below.

Also located in the upper housing 42 as shown in FIG. 6 is a switch 84. When the first arm 78 is moved by the lock 74 from the unlocked position to the locked position, the switch 84 will close. The switch 84 is connected by a wire 86 to a cable 88, which leads to a connector 90 which may in turn be plugged into the input connector 32 on the main pump unit 20. The security containment device 40 will prevent the main pump unit 20 from delivering medication unless the switch 84 has closed to indicate the security containment device 40 has been locked. Actuation of the switch 84 indicating that the security containment device 40 is locked also serves to prevent further settings from being made for the infusion parameters for channel C of the security containment device 40. The switch 84 may optionally be a momentary contact switch which closes for a moment when contacted by the first arm 78.

Also connected to the cable 88 is a wire 92 leading to a socket 94 mounted in the side of the upper housing 42. A plug 96 on a removeable actuation cable 98 is removably plugged into the socket 94 to connect the removeable actuation cable 98 to the security containment device 40. A switch 100 is located at the end of the removeable actuation cable 98 opposite the plug 96, and the switch may be actuated by a patient to request a demand dose or bolus. The removeable actuation cable 98 is of sufficient length to reach a patient, so that the patient need only squeeze a button 102 on the switch 100 to request a demand dose or bolus.

Referring now to FIGS. 10-12, a syringe retainer 104 mounted inside 42 is illustrated. In the preferred embodiment the syringe retainer 104 is hingeably mounted together with the lower housing 44 on the lower back of the upper housing 44. A spring 106 is used to bias the syringe retainer 104 upwardly. The syringe retainer 104 is U-shaped, and is hingeably mounted on the bottom of the U. The upper leg of the U is shorter than is the lower leg. The upper leg of the U is a rectangular plate 108 fitting in the bottom of the opening 46 in the upper housing 42.

The rectangular plate 108 has a notch 110 therein from the front, the notch 110 being to accommodate and support the end of a syringe 111 (FIG. 12) having a luer connector thereon. The lower leg of the U has an aperture 112 therein, which aperture 112 is disposed near the bottom of the U and extends longitudinally in the lower leg of the U. The aperture 112 is to allow the inlet tube 26 to extend downward from the syringe 111 to the interior of the lower housing 44, from which it exits through the notch 72 (FIG. 8B) toward the cassette 22.

The security containment device 40 is intended to accommodate a variety of interchangeable storage compartments, all of which have a rectangular cross-section and fit in the opening 46. Consider first a rectangular syringe tube 120, the bottom of which is shown in FIG. 12. An indentation 122 in the bottom of the rectangular syringe tube 120 is aligned with the slot 82 in the front of the opening 46 in the upper housing 42 when the rectangular syringe tube 120 is inserted fully into the opening 46. The second arm 80 will move into the indentation 122 in the rectangular syringe tube 120 when the lock 74 is moved to the locked position, securing the rectangular syringe tube 120 to the security containment device 40. All interchangeable storage compartments have such an indentation 122, thereby allowing them to be locked to the security containment device 40 to secure medication contained therein.

Alternately, the storage compartments may use one-way snap locks which can only be released from the device when the security containment device is unlocked and released from the inside. Such snap locks are well known in the art.

Referring now to FIG. 14, the rectangular syringe tube 120 is shown with a long end cap 126, which would be adhesively and permanently attached to the rectangular syringe tube 120. The combination of the rectangular syringe tube 120 and the long end cap 126 allow a large syringe 111 to fit therein with the plunger fully extended. If a smaller syringe (not shown) is to be used, a short end cap 128 as shown in FIG. 13 may be used.

Referring now to FIG. 13, if a plastic medication bag 130 is to be used, a bag tube 132 is used in conjunction with the short end cap 128. A needle 134 is attached to the inlet tube 26, and the needle 134 may be inserted into the plastic medication bag 130. Note that all storage compartments used in conjunction with the security containment device 40 will be open only at the end inserted into the opening 46 in the upper housing 42, and that the indentation 122 is present to allow each of the storage compartments to be locked to the security containment device 40.

Installation of the security containment device 40 onto the main pump unit 20 is quick and convenient. The knob 58 is first substituted for the standard bolt on the right side of the main pump unit 20. The lock 74 is turned to the unlocked position, the lower housing 44 is opened, and the lock 74 is returned to the locked position. The slot 50 in the upper housing 42 is placed over the shaft of the knob 58, and the knob 58 is tightened. The lock 74 is then turned again to the unlocked position. The connector 90 is plugged into the input connector 32 on the main pump unit 20, and the plug 96 on the removeable actuation cable 98 is plugged into the socket 94.

The inlet tube 26 from the cassette 22 is threaded through the aperture 112 and the notch 110 in the syringe retainer 104. The desired medication reservoir device is installed into the corresponding storage compartment, the inlet tube 26 is attached to the medication reservoir device, and the storage compartment is inserted fully into the opening 46 in the upper housing 42. The cassette 22 may then be primed and installed onto the main pump unit 20. The lower housing 44 is then closed with the inlet tube 26 extending through the notch 72 in the lower housing 44. The lock 74 is turned to the locked position. The security containment device 40 is properly installed, and the PCA system is ready to be utilized.

As an alternative to the preferred embodiment, it may be desirable in some cases to minimize parts. The latch member 62 and the spring 64 may be deleted by lowering the position of the first arm 78 to the level of the notch 68 in the lower housing 44. It will be appreciated in this case that the first arm 78 will cooperate with the notch 68 in the lower housing 44 to hold the lower housing 44 in a closed position when the lock 74 is in the locked position. When the lock 74 is turned to an unlocked position, the first arm 78 will move out of the notch 68 in the lower housing 44, immediately releasing the lower housing 44 and allowing it to open.

It may thus be perceived from the detailed description of the present invention above that it provides a mechanism for securing the supply of medication in the reservoir located near the PCA pump. The reservoir is secured to the PCA pump to prevent it from being stolen or removed. With the main pump unit secured to an IV post, the present invention by securing the medication to the main pump unit effectively prevents its theft or removal.

In order to make the entire fluid system secure, the system of the present invention also protects the integrity of the fluid line between the medication reservoir and the cassette, thereby preventing an unauthorized individual from breaching the fluid line between the medication reservoir and the cassette and draining the medication reservoir. The present invention prevents the unauthorized removal of the cassette from the main pump unit, thus also preventing a potentially deadly free flow condition through the cassette from occurring.

The security provisions of the present invention thereby prevent both action by a patient or tampering by an unauthorized individual from violating the security of the medication being administered. The security attachment of the present invention is compact in size, inexpensive to manufacture, and yet will accommodate any of the several different sizes and configurations of medication containers, including various size syringes and small flexible plastic bags. Finally, the system of the present invention accomplishes all of the aforesaid objectives and advantages without incurring any relative disadvantage.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modification, and alterations should therefore be seen as within the scope of the present invention.

What is claimed is:

1. An instrument for securely storing fluid medication for use in an infusion pump having a housing and using a replaceable cassette having a fluid inlet and a fluid outlet, comprising:
   a first housing member;
   means for attaching said first housing member to said infusion pump housing;
   a second housing member, said first and second housing members defining a space therebetween, said second housing member being moveable between a first position allowing access to said space defined by said first and second housing members and a second position preventing access to said space defined by said first and second housing members;
   means for receiving a container in which said fluid medication is stored, said receiving means being mounted on said first housing member;
   first locking means for preventing said first housing member from being removed from said infusion pump;
   second locking means for preventing said receiving means from being removed from said first housing member; and
   third locking means mounted on said second housing member for preventing a cassette from being removed from said infusion pump when said second housing member is in said second position.

2. An instrument as defined in claim 1, wherein said first and second housing members are hingedly connected.

3. An instrument as defined in claim 1, wherein said third locking means comprises:
   an extension member mounted on and moveable with said second housing member, said extension member being located directly in front of at least a portion of said cassette when said cassette is mounted in said infusion pump and when said second housing member is in said second position, said extension member thereby preventing said cassette from being removed from said infusion pump when said second housing member is in said second position.

4. An instrument as defined in claim 1, additionally comprising:
   a switch;
   first electrical cable means for connection at one end thereof to said switch, said first electrical cable means having at the other end thereof a first electrical connector; and
   second electrical cable means for connection at one end thereof to a second electrical connector, said second electrical connector being connectable to said first electrical connector, said second cable means for connection at the other end thereof to said infusion pump.

5. An instrument as defined in claim 1, wherein said second housing member is arranged and configured to enclose a fluid line extending between said container in which fluid medication is stored and said cassette when said second housing member is in said second position.

6. An instrument as defined in claim 1, wherein said first housing member has a notch therein, said attaching means comprising:
a knob which has a shaft which may be turned to screw into said infusion pump, said notch in said first housing member being placed over said shaft of said knob between said knob and said infusion pump, said knob being turned to tighten said first housing member against said infusion pump.

7. An instrument as defined in claim 6, wherein said first locking means comprises:
fourth means for locking said second housing member in said second position with respect to said first housing member.

8. An instrument as defined in claim 7, wherein said fourth locking means comprises:
a notch located in said second housing member;
a latch mounted in said first housing member, said latch being moveable between a locked position in which said latch engages said notch in said second housing member to retain said second housing member in said second position with respect to said first housing member and an unlocked position in which said latch is disengaged from said second housing member to allow said second housing member to move to said first position with respect to said first housing member.

9. An instrument as defined in claim 8, wherein said fourth locking means additionally comprises:
a lock mounted in said first housing member and having a first arm moveable between a locked position and an unlocked position, said first arm bearing against said latch when said first arm is in said locked position to prevent said latch from being moved from said locked position of said latch to said unlocked position of said latch.

10. An instrument as defined in claim 9, wherein said first arm of said lock bears against said knob when said first arm is in said unlocked position to prevent said knob from being turned to remove said instrument from said infusion pump.

11. An instrument as defined in claim 9, additionally comprising:
switch means actuated by said first arm when said first arm is in said locked position.

12. An instrument as defined in claim 1, wherein said receiving means comprises:
a storage compartment open at one end thereof, said storage compartment for receiving and holding therein a container in which said fluid medication is stored; and
means, located in said first housing member, for receiving said open end of said storage compartment.

13. An instrument as defined in claim 12, wherein said means for receiving said open end of said storage compartment comprises:
an aperture located in said first housing member, said aperture being arranged and configured to receive said open end of said storage compartment therein.

14. An instrument as defined in claim 13, wherein said second locking means comprises:
a notch in the portion of said storage compartment received in said aperture located in said first housing member; and
a lock mounted in said first housing member and having a second arm moveable between a locked position and an unlocked position, said second arm engaging said notch in said storage compartment when said second arm is in said locked position, said second arm preventing said storage compartment from being removed from said aperture located in said first housing member when said second arm is engaging said notch in said storage compartment.

15. An instrument as defined in claim 12, wherein said storage compartment is arranged and configured to hold a syringe.

16. An instrument as defined in claim 12, wherein said storage compartment is arranged and configured to hold a plastic medicine bag.

17. An instrument as defined in claim 12, wherein said receiving means additionally comprises:
retainer means for supporting a syringe, said retainer means being located inside said first housing member, a syringe located in said storage compartment resting on said retainer means when said storage compartment is received by said receiving means located in said first housing member.

18. An instrument as defined in claim 12, wherein said first locking means comprises:
a lock mounted in said first housing member, said lock for driving a lock shaft between a locked position and an unlocked position; and
a first arm mounted on and moveable with said lock shaft, said first arm causing said second housing member to be retained in said second position when said second housing member is first in said second position with respect to said first housing member and said lock shaft is then moved from said unlocked position to said locked position; and wherein said second locking means comprises:
a second arm mounted on and moveable with said lock shaft, said second arm causing said storage compartment to be retained in said means for receiving said open end of said storage compartment in said first housing member when said storage compartment is first inserted into said means for receiving said open end of said storage compartment and said lock shaft is then moved from said unlocked position to said locked position.

19. An instrument for securely storing a container of fluid medication for use in an infusion pump having a housing and using a replaceable cassette having a fluid inlet tube and a fluid outlet tube, said instrument comprising:
a first housing member;
a second housing member moveable with respect to said first housing member between a first position in which a cassette may be removed from said infusion pump and a second position in which said cassette may not be removed from said infusion pump;
means for attaching said first housing member to said infusion pump housing;
means for receiving a container in which said fluid medication is stored, said receiving means being mounted on said first housing member;

first locking means for preventing said first housing member from being removed from said infusion pump;

second locking means for preventing said receiving means from being removed from said first housing member; and third locking means for retaining said second housing member in said second position to prevent said cassette from being removed from said infusion pump.

20. An instrument as defined in claim 19, wherein said second housing member is arranged and configured to enclose a fluid line extending between said container in which fluid medication is stored and said cassette when said second housing member is in said second position.

21. An instrument for securely storing fluid medication for use in an infusion pump having a housing and using a replaceable cassette having a fluid inlet and a fluid outlet, comprising:

a housing;

means for attaching said housing to said infusion pump housing;

means for receiving a container in which said fluid medication is stored;

first locking means for preventing said housing from being removed from said infusion pump;

second locking means for securing said receiving means to said housing; and third locking means mounted on said housing for preventing a cassette from being removed from said infusion pump.

22. An instrument as defined in claim 21, wherein said housing is arranged and configured to enclose a fluid line extending between said container in which fluid medication is stored and said cassette when said second housing member is in said second position.

23. A method for securing fluid medication for use in an infusion pump having a housing and using a replaceable cassette having a fluid inlet and a fluid outlet, comprising:

mounting a first housing member on said infusion pump housing;

hingedly mounting a second housing member onto said first housing member, said first and second housing member defining a space therebetween, said second housing member being moveable between a first position allowing access to said space defined by said first and second housing members and a second position preventing access to said space defined by said first and second housing members;

mounting a container in which said fluid medication is stored on said first housing member;

first, preventing said first housing member from being removed from said infusion pump with first locking means;

second, preventing said receiving means from being removed from said first housing member with second locking means; and third, preventing said cassette from being removed from said infusion pump when said second housing member is in said second position with third locking means mounted on said second housing member.

24. An instrument as defined in claim 23, additionally comprising:

enclosing a fluid line extending between said container in which fluid medication is stored and said cassette with said second housing member when said second housing member is in said second position.

* * * * *